United States Patent [19]

Hovey et al.

[11] 4,215,010
[45] Jul. 29, 1980

[54] PHOTOCHROMIC COMPOUNDS

[75] Inventors: Richard J. Hovey, Sturbridge; Nori Y. C. Chu, Southbridge; Peter G. Piusz, Longmeadow, all of Mass.; Charles H. Fuchsman, Bemidji, Minn.

[73] Assignee: American Optical Corporation, Southbridge, Mass.

[21] Appl. No.: 940,535

[22] Filed: Sep. 8, 1978

[51] Int. Cl.² .......................... G02B 5/23; G02B 1/04; C07D 265/38
[52] U.S. Cl. .................... 252/300; 350/354; 544/71; 430/345; 252/600
[58] Field of Search .......... 252/300; 544/71; 96/90 PC; 350/354

[56] References Cited

U.S. PATENT DOCUMENTS

| | | | |
|---|---|---|---|
| 3,562,172 | 2/1971 | Ono et al. | 252/300 |
| 3,578,602 | 5/1971 | Ono et al. | 252/300 |
| 4,046,586 | 9/1977 | Uhlmann et al. | 252/300 |

FOREIGN PATENT DOCUMENTS

| | | | |
|---|---|---|---|
| 659801 | 2/1965 | Belgium | 252/300 |
| 1927849 | 12/1970 | Fed. Rep. of Germany | 544/71 |

*Primary Examiner*—Richard E. Schafer
*Assistant Examiner*—Deborah L. Kyle
*Attorney, Agent, or Firm*—Jeremiah J. Duggan; Alan H. Spencer; Stephen A. Schneeberger

[57] ABSTRACT

Photochromic compounds of the formula

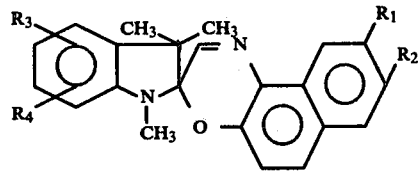

wherein one of $R_1$ and $R_2$ is halogen or lower alkoxy, and the other is hydrogen, and $R_3$ and $R_4$ are hydrogen, lower alkyl, lower alkoxy, or halogen and their use in lenses are disclosed.

14 Claims, No Drawings

PHOTOCHROMIC COMPOUNDS

BACKGROUND OF THE INVENTION

This invention relates to spirooxazine photochromic compounds having a particular utility in fabricating photochromic sunglass lenses and the like.

1,3,3-trimethylspiro[indoline-2,3'-[3H]naphth-[2,1-b][1,4])oxazines] are known photochromic compounds. The change in optical density between the unactivated and activated states as measured at the wavelength of maximum absorption ranges from about 0.43 to about 0.89 for some of the disclosed species. Such compounds are disclosed in U.S. Pat. No. 3,578,602 to Ono et al, entitled "Photochromic Compound". Another Ono et al patent U.S. Pat. No. 3,562,172 discloses similar compounds.

SUMMARY OF THE INVENTION

In accordance with the instant invention, it has been found that the substitution of a methoxy group, ethoxy group or halogen in the 8' or 9'-position of 1,3-dimethyl-3-methylspiro[indoline-2,3'-[3H]-naphth [2,1-b][1,4]oxazine] derivatives having substituents on the indoline ring results in photochromic compounds having enhanced photocolorability, or a relatively large change in optical density between the activated and unactivated state, and yet are also characterized by enhanced luminous transmittance, about 80% or more, in the unactivated state. Furthermore, it has been discovered that the photochromic compounds of the invention may be incorporated within optically clear plastics such as poly(allyl diglycol carbonate), polyacrylates, polymethacrylates, cellulose acetate, cellulose triacetate, cellulose acetate propionate, cellulose acetate butyrate, poly(vinylacetate), poly(vinylalcohol), polyester resins, and preferably poly(allyl diglycol carbonate), polycarbonate, poly(methylmethacrylate), and cellulose acetate butyrate or propionate to make a photochromic element suitable for a photochromic sunglass lens, ski goggle, or the like.

The compounds of the present invention may be synthesized using the procedure disclosed by Ono et al using starting materials having appropriate substitutions.

In an alternative procedure the indoleninium iodide corresponding to the respective methylene indoline compound can be used along with triethylamine. Both procedures are suitable for the production of the desired photochromic compounds. We prefer to recrystalize from acetone rather than the ethyl alcohol of Ono et al.

Accordingly, it is an object of the invention to provide a novel class of photochromic spirooxazine compounds. Another object of the invention is to provide a class of photochromic spirooxazine compounds having enhanced photo-colorability and yet a relatively high luminous transmittance in the unactivated state. Still another object of the invention is to provide sunglass lenses and the like having improved photochromic response.

DESCRIPTION OF THE PREFERRED EMBODIMENT

The invention provides a class of novel photochromic compounds represented by the structural formula:

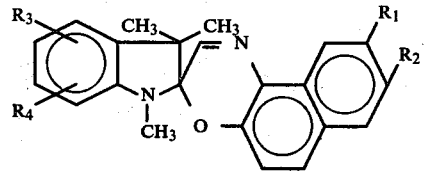

wherein one of $R_1$ and $R_2$ is halogen or lower alkoxy, and the other is hydrogen, and $R_3$ and $R_4$ are hydrogen, lower alkyl, lower alkoxy or halogen.

Between 0.1 and about 15 weight percent of the compound may then be incorporated into an optically clear plastic film to produce a photochromic element having high luminous transmittance in the unactivated state and enhanced photocolorability. The optically clear matrix will preferably have a thickness in the range of 0.0001–1.0 inch. For a film 0.006 inches thick, 2% by weight of the photochromic spirooxazine compounds of the invention is a preferred formulation. The dyes of the invention may be also mixed with an optically clear polymer which is thereafter cast as a film or lens, a polymer which is injection molded or otherwise shaped into a film or lens; or the dyes may be dissolved in a solution of alcohol, water or the like and then imbibed into a prepolymerized film, or lens. Preferred solvents are polyhydric alcohols, especially diethylene glycol or other polyethylene glycols. Poly(allyl diglycol carbonate), polycarbonate, polymethacrylate, cellulose acetate, cellulose triacetate, cellulose acetate propionate, cellulose acetate butyrate, poly(vinylacetate), poly(vinylalcohol), copolymers and mixtures thereof may be used. However, the preferred materials for use as a host for the compounds of the invention are poly(allyl diglycol carbonate), polycarbonate, poly(methylmethacrylate), and cellulose acetate butyrate or propionate. Such films or lens elements may be used as sunglass lenses, ski goggles or the like which have a high luminous transmittance in the unactivated state, yet darken significantly in the presence of sunlight.

EXAMPLE I 40 grams of the 1-nitroso-7-methoxy-2-naphthol was dissolved in 400 ml of ethanol. $N_2$ gas was bubbled into the system, which was then heated to a gentle reflux at about 70° C. A solution of 65 grams of 1,2,3,3,4(and 6), 5-hexamethyl indoleninium iodide in 200 ml of ethanol containing 24 grams of trimethylamine was added over a thirty minute period. After the mixture was refluxed for two hours, the solution was then cooled and the brown precipitate separated by filtering. The weight of crude 1,3,3,4(and 6), 5-pentamethyl-9'-methoxy-spiroindoline-naphthoxazine obtained was 29 grams. The crude product was purified by recrystallization from acetone.

A 4% by weight solution of the dye in diethylene glycol was heated to 120° C. Following immersion in the hot dye solution for 1½ hours, a cast plano CR-39 lens 2 mm thick had the following transmission properties at 72° F.

TABLE I

| Activating Light Intensity (microwatts cm$^{-2}$)[1] | Luminous Transmittance (%) | Transmittance At λ max(600 NM) |
|---|---|---|
| 320 | 78.7 | 73.6 |
| 820 | 58.3 | 41.7 |
| 1250 | 50.8 | 31.8 |

TABLE I-continued

| Activating Light Intensity (microwatts cm$^{-2}$)[1] | Luminous Transmittance (%) | Transmittance At λ max(600 NM) |
|---|---|---|
| 2150 | 37.7 | 17.5 |
| 3250 | 28.0 | 8.6 |
| 4350 | 21.0 | 3.8 |
| 5740 | 17.5 | 1.5 |

[1] For light of wavelengths between 300-400 nanometers.

Similar results are obtained using polycarbonate, polymethylmethacrylate when imbibed with a dye according to the present invention.

EXAMPLE II

A series of comparisons were conducted to demonstrate that the claimed class of compounds had substantially enhanced photocolorability (ΔOD) over a compound having the same indoline substituents but not having a substituent on the naphthalene group. Each test was conducted by compounding 2 weight percent of the specified dye with cellulose acetate butyrate and casting a film therewith. Each cast film was approximately 6 mils thick. The percent of light transmitted through the unactivated film was then measured. The films were then activated using a 100 watt mercury vapor source and the change in optical density (ΔOD)determined. The test results reported in the following table were obtained at about 23° C.±1.5° C. with a light intensity of 6700 microwatts per sq. cm. at a wavelength of 300-400 n.m.

TABLE II

| | $R_1$ & $R_2$ = H (Prior Art) | | | $R_1$ = methoxy | | | $R_1$ = ethoxy | | | $R_2$ = Bromo | | |
|---|---|---|---|---|---|---|---|---|---|---|---|---|
| $R_3$ and/or $R_4$ = | F.T. (mils) | % L.T. | ΔOD at λmax | F.T. (mils) | % L.T. | ΔOD at λmax | F.T. (mils) | % L.T. | ΔOD at λmax | F.T. (mils) | % L.T. | ΔOD at λmax |
| H | 6.0 | 88 | 0.9 | 4.7 | 88 | 1.4 | 5.9 | 88 | 1.4 | 3.6 | 86 | 1.2 |
| 5-methyl | 6.0 | 87 | 1.4 | 6.0 | 86 | 1.8 | | | | | | |
| 6-methyl | 6.3 | 88 | 1.1 | 6.0 | 88 | 1.8 | | | | | | |
| 7-methyl | 6.2 | 87 | 0.8 | 6.1 | 87 | 1.3 | | | | | | |
| 4,5-dimethyl | | | | 6.1 | 78 | 3.3 | | | | | | |
| 4(and 6),5-dimethyl | 7.5 | 81 | 1.1 | 6.1 | 78 | 2.6 | | | | 6.1 | 82 | 3.8 |
| 4,7-dimethyl | 6.6 | 85 | 1.3 | 4.8 | 86 | 1.9 | | | | | | |
| 5,6-dimethyl | | | | 6.1 | 84 | 2.2 | | | | | | |
| 5,7-dimethyl | | | | 6.0 | 84 | 1.6 | | | | | | |
| 6,7-dimethyl | | | | 6.3 | 85 | 1.5 | | | | | | |
| 5-methoxy | | 81 | 2.7 | 6.1 | 83 | 2.3 | | | | | | |
| 4,7-dimethoxy | 6.2 | 87 | 1.2 | 6.3 | 85 | 2.0 | | | | | | |
| 5-chloro | 4.9 | 89 | 0.9 | 5.3 | 88 | 1.2 | | | | | | |

What is claimed is:

1. A compound having the formula;

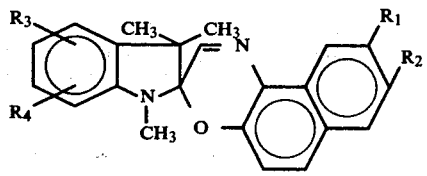

wherein one of $R_1$ and $R_2$ is halogen or lower alkoxy, and the other is hydrogen, and $R_3$ and $R_4$ are hydrogen, lower alkyl, lower alkoxy, or halogen.

2. The compound according to claim 1 wherein $R_1$ is hydrogen.

3. The compound according to claim 1 wherein $R_2$ is hydrogen.

4. The compound according to claim 1 wherein $R_1$ is methoxy.

5. The compound according to claim 1 wherein $R_3$ is hydrogen.

6. The compound according to claim 1 wherein $R_3$ and $R_4$ are methyl.

7. The compound according to claim 1 wherein $R_2$ is halogen.

8. The compound according to claim 6 wherein $R_1$ is methoxy.

9. The compound according to claim 6 wherein $R_2$ is halogen.

10. A photochromic optical element comprising, (A) a transparent plastic host and (B) an effective amount of photochromic compound selected from the group consisting of 1,3,3-trimethyl-9'-methoxy-; 1,3,3-trimethyl-9'-ethoxy-; 1,3,3-trimethyl-8'-bromo-; 1,3,3,5-tetramethyl-9'-methoxy-; 1,3,3,6-tetramethyl-9'-methoxy-; 1,3,3,7-tetramethyl-9'-methoxy-; 1,3,3,4,5-pentamethyl-9'-methoxy; 1,3,3,5,6-pentamethyl-9'-methoxy-; 1,3,3,4,7-pentamethyl-9'-methoxy-; 1,3,3,5,7-pentamethyl-9'-methoxy-; 1,3,3,6,7-pentamethyl-9'-methoxy-; 1,3,3-trimethyl-5,9'-dimethoxy-; 1,3,3-trimethyl-4,7,9'-trimethoxy-; 1,3,3-trimethyl-5-chloro-9'-methoxy-; 1,3,3,4,5-pentamethyl-8'-bromo-; 1,3,3,5,6-pentamethyl-8'-bromo-spiroindolinenaphthooximes and mixtures thereof.

11. The photochromic optical element according to claim 10 wherein the element is a lens and the host is polycarbonate resin.

12. The photochromic optical element according to claim 10 wherein the element is an ophthalmic lens and the host is poly(allyl diglycol carbonate).

13. The element according to claim 10 wherein the element is an ophthalmic lens and the host is cellulose acetate butyrate.

14. The element according to claim 10 wherein the element is an ophthalmic lens and the host is cellulose acetate propionate.

* * * * *